(12) United States Patent
Bormann et al.

(10) Patent No.: US 6,231,770 B1
(45) Date of Patent: May 15, 2001

(54) MULTIPLE ELEMENT FILTER AND METHOD OF USING THEREFOR

(75) Inventors: Thomas J. Bormann, Melville; Gerard R. DelGiacco, Yonkers; Vlado I. Matkovich, Glen Cove, all of NY (US); Mladen Franovic, Cos Cob, CT (US)

(73) Assignee: Pall Corporation, East Hills, NY (US)

( * ) Notice: Subject to any disclaimer, the term of this patent is extended or adjusted under 35 U.S.C. 154(b) by 0 days.

(21) Appl. No.: 09/214,415

(22) PCT Filed: Jul. 3, 1997

(86) PCT No.: PCT/US97/11733

§ 371 Date: Mar. 18, 1999

§ 102(e) Date: Mar. 18, 1999

(87) PCT Pub. No.: WO98/01207

PCT Pub. Date: Jan. 15, 1998

Related U.S. Application Data
(60) Provisional application No. 60/021,394, filed on Jul. 9, 1996.

(51) Int. Cl.[7] ............................ B01D 37/00; B01D 29/00
(52) U.S. Cl. ........................ 210/767; 210/420; 210/422; 210/428; 210/436; 210/456; 210/472
(58) Field of Search ................................. 210/420, 422, 210/428, 436, 438, 439, 446, 456, 472, 767

(56) References Cited

U.S. PATENT DOCUMENTS

| | | | |
|---|---|---|---|
| 4,009,714 | 3/1977 | Hammer | 210/445 |
| 4,009,715 * | 3/1977 | Forberg et al. | 210/455 |
| 4,021,353 | 5/1977 | Raines et al. | 210/448 |
| 4,056,476 | 11/1977 | Mouwen et al. | 210/446 |
| 4,267,053 | 5/1981 | Hashino et al. | 210/650 |
| 4,304,670 | 12/1981 | Watanabe et al. | 210/446 |
| 4,369,112 | 1/1983 | Vincent et al. | 210/433.2 |
| 4,422,939 | 12/1983 | Sharp et al. | 210/445 |
| 4,601,820 | 7/1986 | Leason | 210/94 |
| 4,783,259 * | 11/1988 | Wade | 210/497.1 |
| 4,880,548 | 11/1989 | Pall et al. | 210/767 |
| 4,904,384 * | 2/1990 | Potz | 210/323.2 |
| 4,925,572 * | 5/1990 | Pall | 210/767 |
| 4,963,260 | 10/1990 | Naoi et al. | 210/446 |
| 5,069,789 | 12/1991 | Mohn et al. | 210/321.84 |
| 5,096,582 | 3/1992 | Lombardi et al. | 210/321.6 |
| 5,152,890 * | 10/1992 | Linnerstein | 210/497.01 |
| 5,152,905 | 10/1992 | Pall et al. | 210/767 |
| 5,244,578 | 9/1993 | Ohnishi et al. | 210/650 |
| 5,302,354 * | 4/1994 | Watvedt et al. | 210/493.5 |
| 5,342,517 | 8/1994 | Kopf | 210/228 |
| 5,439,587 | 8/1995 | Stankowski et al. | 210/321.64 |
| 5,451,321 | 9/1995 | Matkovich | 210/641 |
| 5,472,605 | 12/1995 | Zuk et al. | 210/436 |
| 5,622,626 * | 4/1997 | Matkovich et al. | 210/649 |
| 5,823,229 * | 10/1998 | Bertrand et al. | 210/449 |

FOREIGN PATENT DOCUMENTS

| | | |
|---|---|---|
| 0 122 748 | 10/1984 | (EP) . |
| 0 333 119 | 9/1989 | (EP) . |
| WO 95/21644 | 8/1995 | (WO) . |

\* cited by examiner

*Primary Examiner*—John Kim
(74) *Attorney, Agent, or Firm*—Leydig, Voit & Mayer, Ltd.

(57) ABSTRACT

A biological fluid filter assembly (100) including a plurality of porous media (6a, 6b) and essentially lacking a solid partition between the media is disclosed. Preferably, the assembly has a space (12) between the media (6a, 6b). The filter assembly is especially suitable for depicting leukocytes from a biological fluid such as packed red cells, and can be used to deplete leukocyts from two or more units of biological fluid. A method of using the filter assembly is also provided.

47 Claims, 6 Drawing Sheets

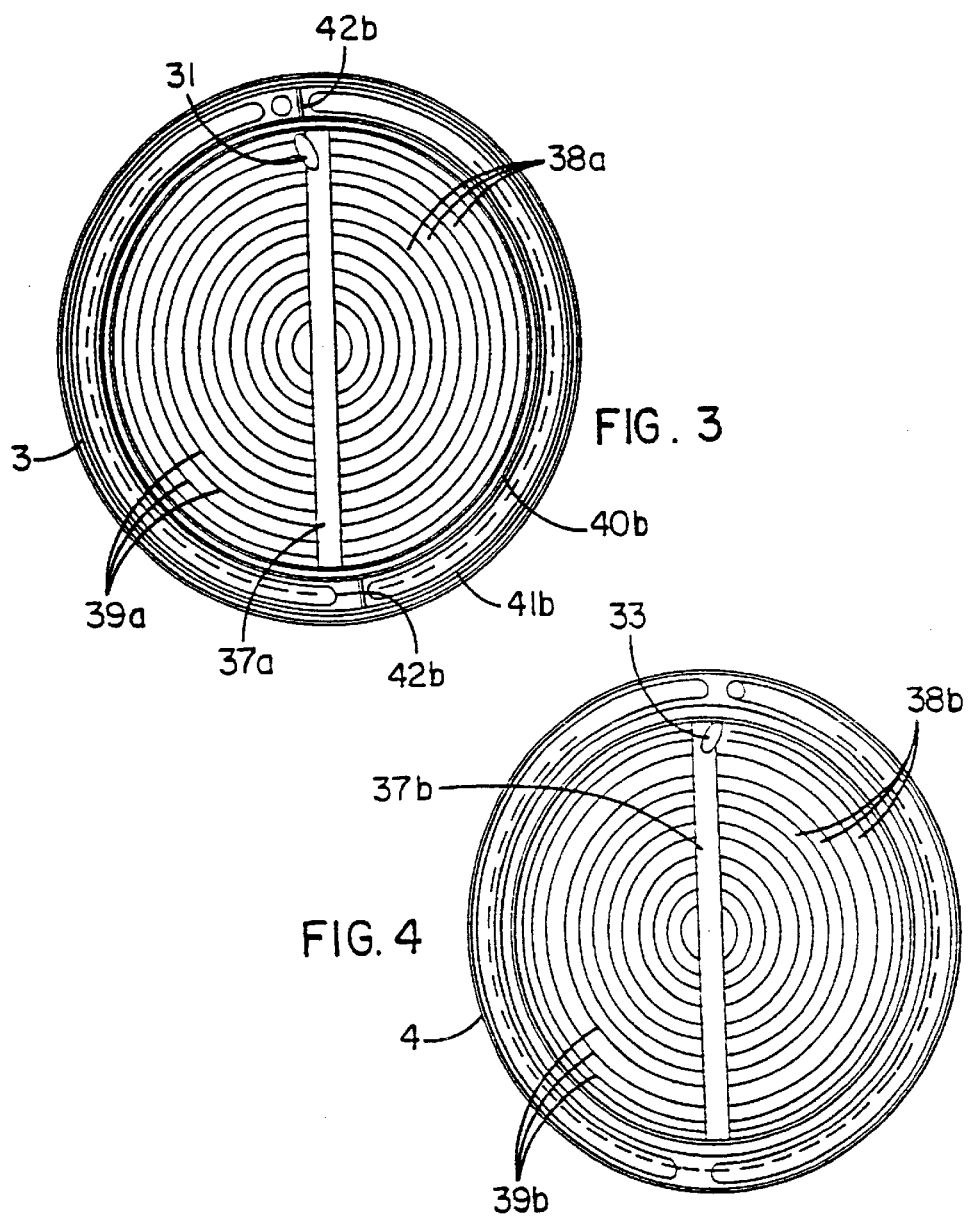
FIG. 3
FIG. 4
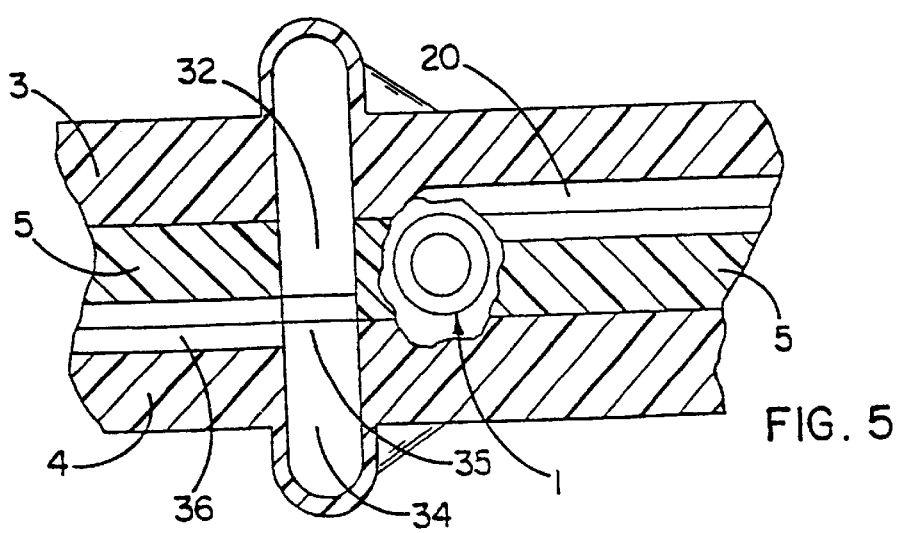
FIG. 5

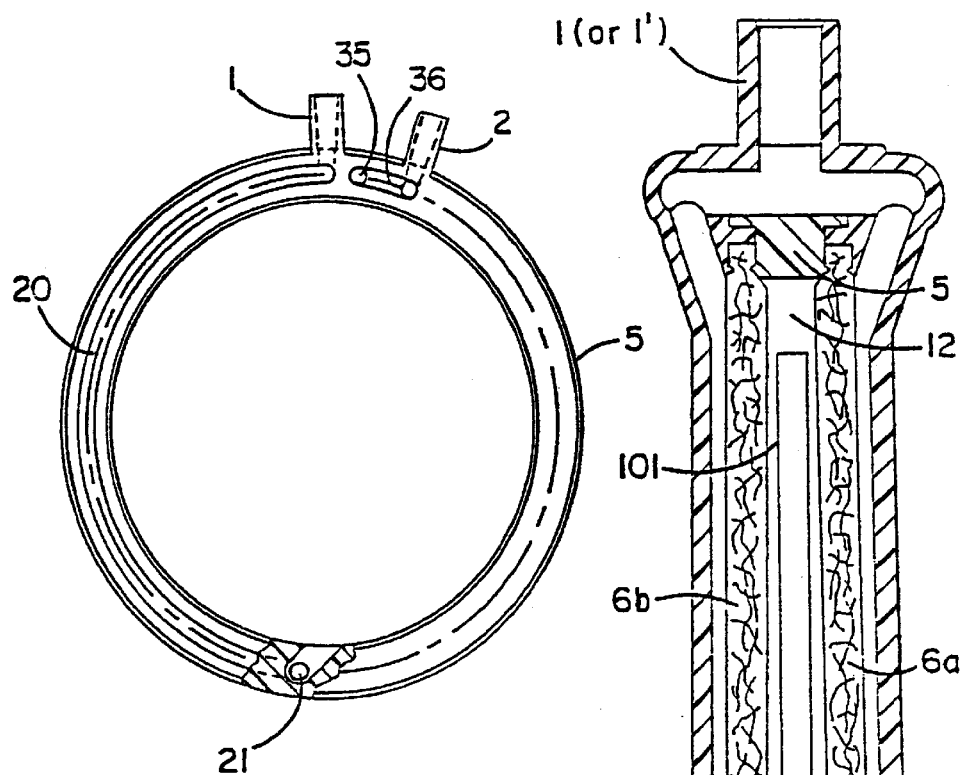
FIG. 6
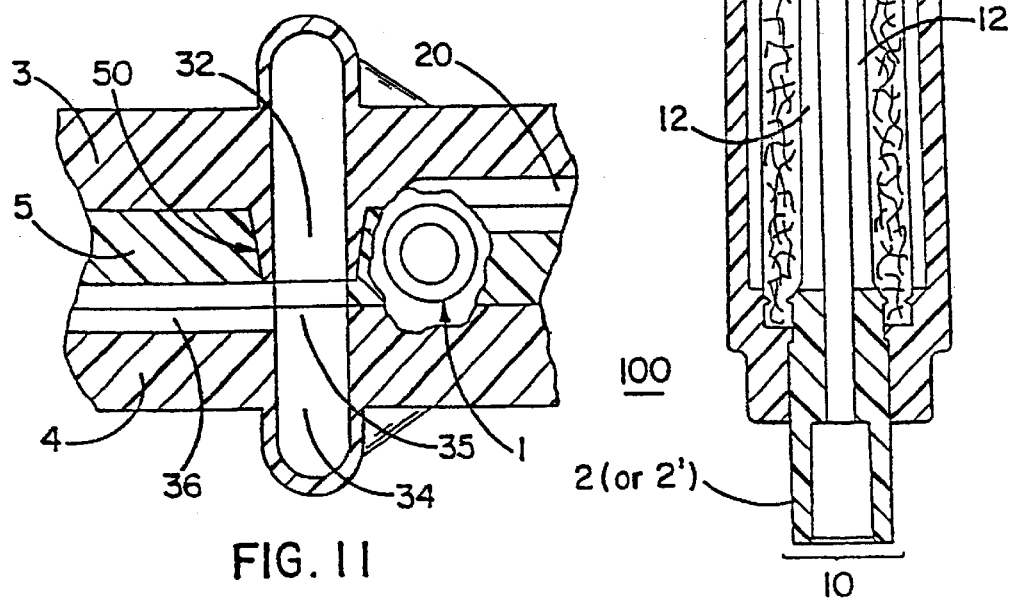
FIG. 11
FIG. 7

MULTIPLE ELEMENT FILTER AND
METHOD OF USING THEREFOR

This application claims the benefit of U.S. provisional patent application 60/021,394, filed Jul. 9, 1996, which is incorporated by reference in its entirety.

This application is filed under 35 U.S.C. 371 of PCT/US97/11733 filed Jul. 3, 1997.

TECHNICAL FIELD

This invention relates to the processing of biological fluids such as blood and blood components, particularly to remove undesirable material such as leukocytes from the biological fluid.

BACKGROUND OF THE INVENTION

Many biological fluid processing protocols include filtering the fluid before use. For example, a biological fluid such as blood or at least one blood component can be filtered to remove undesirable material such as debris, gels, microaggregates and/or leukocytes before transfusing the biological fluid. In some protocols, for example, involving bedside administration of blood or blood components, two or more units of blood components such as red blood cells or platelet concentrate can be leukocyte depleted and administered.

However, some of these protocols have suffered from a number of drawbacks. For example, some filters have suffered from clogging, which can prevent or delay the administration of the desired number of units. Alternatively, the use of a separate filter for each unit of blood or blood component can be time consuming, since each filter has to be attached to the blood processing system, and primed. Additionally, some fluid remains in each filter after filtration, and is not transfused to the patient. Thus, the cumulative loss of this held up fluid can be significant.

In an attempt to overcome the problem of clogging, some filter devices include two filter elements, separated by a partition plate, in a single housing. The elements are pressed against the opposite sides of the partition plate, and the elements can be sealed to the opposing sides of the plate. In typical use, blood enters the top of the device, and contacts the partition plate. The blood is then directed to, and passes through, a filter element. The filtered blood subsequently exists the bottom of the device.

These filter devices have also suffered from a number of problems, particularly with respect to difficulty in priming. Air can be trapped in the device, making it difficult to wet either or both of the filter elements. As a result, it may be difficult to pass blood through the device, or blood may flow through one of the filter elements, and little or no blood flows through the other element. Also, since air is trapped, it can be difficult to efficiently drain the device. Additionally, or alternatively, since the device must be of sufficient size to accommodate two filter elements, the device may retain an undesirably large amount of the valuable blood or blood component.

Another disadvantage of at least some of these filters, e.g., those used with one unit of blood, is that they are difficult to include in a centrifugable blood bag system. For example, the filter may be too large to fit in a centrifuge cup, and/or the filter or blood bags may be damaged during centrifugation.

The present invention provides for ameliorating at least some of the disadvantages of the prior art. These and other advantages of the present invention will be apparent from the description as set forth below.

SUMMARY OF THE INVENTION

In accordance with the present invention, a biological fluid filter device is provided having first and second fluid flow paths, with a first porous medium across the first fluid flow path, and a second porous medium across the second fluid flow path, and a space therebetween, wherein the first surface of the first porous medium opposes, and has at least a portion of the surface spaced apart from, the first surface of the second porous medium, and the device essentially lacks a solid partition between the first and second media. For example, the space between the media, which typically has a dimension that changes (e.g., a tapered diametric cross-sectional area), can be bounded on one side by the first porous medium, and bounded on the other side by the second porous medium.

In some embodiments, a biological fluid filter device is provided having first and second fluid flow paths, with a first porous medium across the first fluid flow path, and a second porous medium across the second fluid flow path, and essentially lacking a solid partition between the first and second media. The device can also include at least one element such as a screen or spacer that is capable of allowing biological fluid flow therethrough, interposed between the first and second porous media. For example, the device can include a first screen upstream of the first porous medium, and a second screen upstream of the second porous medium, and the device can also include a space between the first and second porous media, wherein the space is bounded on one side by the first screen, and bounded on the other side by the second screen. In a more preferred embodiment, the first and second porous media each comprise a leukocyte depletion medium.

In another embodiment of the invention, a biological fluid filter device is provided comprising a housing having an inlet and an outlet and defining at least one fluid flow path flow path between the inlet and the outlet, and having a porous medium interposed between the inlet and the outlet and across the fluid flow path, wherein the housing includes at least one semicircular fluid flow channel that directs fluid from one end to the housing to the substantially opposite end of the housing before contacting the porous medium and/or directs the fluid passing through the porous medium to the outlet of the device. In one embodiment, the device includes a semicircular fluid flow channel that directs fluid from one end to the housing to the substantially opposite end of the housing before contacting the porous medium and includes another semicircular fluid flow channel that directs the fluid passing through the porous medium to the outlet of the device.

The present invention also provides a method of filtering a biological fluid such as blood or a blood component comprising passing at least one unit of biological fluid through a filter device having first and second fluid flow paths, and a first porous medium across the first fluid flow path, and a second porous medium across the second fluid flow path, and a space between the first and second porous media, wherein the device essentially lacks a solid partition between the media. The method includes passing a portion of the biological fluid along a first fluid flow path through the first porous medium and through the outlet, and, without substantially utilizing a solid partition to separate one portion from another, passing another portion of the biological fluid along a second fluid flow path through the second porous medium and through the outlet. The method can include passing biological fluid through at least one element upstream of the first porous medium and the second porous medium. For example, embodiments of the method include passing a portion of the biological fluid along a first fluid flow path through the first screen and the first porous medium and through the outlet, and passing another portion of the biological fluid along a second fluid flow path through the second screen and the second porous medium and through the outlet.

In some embodiments, the method provides for filtering more than one unit of biological fluid through the same device to remove leukocytes from the multiple units of fluid.

In preferred embodiments according to the invention, the filter device directs unfiltered biological fluid to contact the first and second porous media at the bottom of the housing, and the housing fills from the bottom. The rising front of biological fluid displaces air from the device while minimizing or eliminating the presence of trapped air.

Typically, the device is utilized without prewetting or priming the porous media with a non-biological fluid such as saline or an additive solution.

BRIEF DESCRIPTION OF THE DRAWINGS

FIG. 3 illustrates an elevation view of the inner surface of an outlet section including an outlet fluid flow channel leading from the first porous medium according to an embodiment of the invention.

FIG. 4 illustrates an elevation view of the inner surface of an outlet section including of an outlet fluid flow channel leading from the second porous medium according to an embodiment of the invention.

FIG. 5 illustrates a cross-sectional view along line II—II of FIG. 1A showing an inlet port, as well as a common outlet port communicating with two outlet sections according to an embodiment of the invention.

FIG. 6 illustrates an elevation view of another embodiment of the invention, showing an inlet and an outlet near one end of the device.

FIG. 7 illustrates a cross-sectional side view of another embodiment of the present invention showing first and second porous media in a housing, and including a conduit in the space between the first and second porous media.

FIG. 11 illustrates a cross-sectional view of along line II—II of another embodiment of FIG. 1A showing an inlet port, as well as a common outlet port communicating with two outlet sections according to an embodiment of the invention.

SPECIFIC DESCRIPTION OF THE INVENTION

Figure 1A:
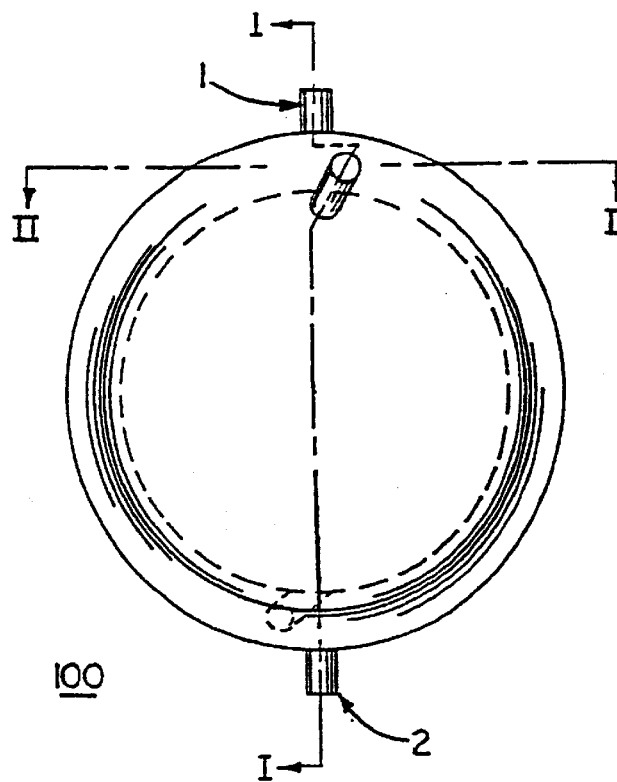
FIG. 1A is a schematic view of an embodiment of a device according to the present invention.

In accordance with embodiments of the invention, a biological fluid filter device is provided comprising a housing having an inlet and an outlet and defining a first fluid flow path and a second fluid flow path between the inlet and the outlet, wherein the housing essentially lacks a solid partition between the first fluid flow path and the second fluid flow path; a first porous medium, having a first surface and a second surface, interposed between the inlet and the outlet and across the first fluid flow path; a second porous medium, having a first surface and a second surface, interposed between the inlet and the outlet and across the second fluid flow path; and a space between the first porous medium and the second porous medium, the first surface of the first porous medium opposing, and, for at least a portion of said surface spaced apart from, the first surface of the second porous medium.

In an embodiment, the device also includes at least one additional element that allows biological fluid to flow therethrough, interposed between the first and second porous media. An exemplary element capable of allowing biological fluid flow therethrough comprises a mesh, a net, a screen, or a perforated plate. For example, the device can include a first screen having a first surface and a second surface, the screen being disposed upstream of the first porous medium, and interposed between the inlet and the outlet and across the first fluid flow path; and a second screen having a first surface and a second surface, the screen being disposed upstream of the second porous medium, and interposed between the inlet and the outlet and across the second fluid flow path. Illustratively, the device can have a space between the first screen and the second screen, the first surface of the first screen opposing, and, for at least a portion of said surface spaced apart from, the first surface of the second screen, wherein the second surface of the first screen contacts the first surface of the first porous medium, and the second surface of the second screen contacts the first surface of the second porous medium.

In another embodiment of the invention, a biological fluid filter device is provided comprising a housing having an inlet and an outlet and defining a first fluid flow path and a second fluid flow path between the inlet and the outlet, wherein the housing essentially lacks a solid partition between the first fluid flow path and the second fluid flow path; a first porous medium, having a first surface and a second surface, interposed between the inlet and the outlet and across the first fluid flow path; a second porous medium, having a first surface and a second surface, interposed between the inlet and the outlet and across the second fluid flow path; and at least one element capable of allowing biological fluid flow therethrough interposed between the first porous medium and the second porous medium. Typically, the device includes a space between the first and second porous media.

In some embodiments, the filter device includes a plurality of elements capable of allowing biological fluid flow therethrough interposed between the first porous medium and a second porous medium. For example, a first element can be disposed upstream of the first porous medium and across the first fluid flow path, and a second element can be disposed upstream of the second porous medium and across the second fluid flow path. In one embodiment, the filter device includes a space between the first and second elements.

Another embodiment of a biological fluid filter device comprises a housing having an inlet and an outlet and defining a first fluid flow path and a second fluid flow path between the inlet and the outlet; a first porous medium, having a first surface and a second surface, interposed between the inlet and the outlet and across the first fluid flow path; a second porous medium, having a first surface and a second surface, interposed between the inlet and the outlet and across the second fluid flow path; and a tapered space between the first porous medium and the second porous medium, the first surface of the first porous medium opposing, and for at least a portion of said surface spaced apart from, the first surface of the second porous medium.

Yet another embodiment of a biological fluid filter device comprises a housing having an inlet and an outlet and defining a first fluid flow path and a second fluid flow path between the inlet and the outlet; a first porous medium, having a first surface and a second surface, interposed between the inlet and the outlet and across the first fluid flow path; a second porous medium, having a first surface and a second surface, interposed between the inlet and the outlet and across the second fluid flow path; and a space between the first porous medium and the second porous medium, the space bounded on one side by the first surface of the first porous medium, and bounded on the other side by the first surface of the second porous medium; wherein a portion of the first surface of the first porous medium contacts a portion of the first surface of the second porous medium. In some embodiments, the space is bounded on one side by the first surface of the first screen and bounded on the other side by the first surface of the second screen; wherein a portion of the first surface of the first screen contacts a portion of the first surface of the second screen.

In accordance with typical embodiments of the invention, the space between the screens or the porous media has a dimension such as area and/or volume that changes from one portion of the device to another. For example, the space can be tapered so that the area of the space decreases from one end of the device to another.

Another embodiment of a biological fluid filter device comprises a housing having an inlet and an outlet and defining at least one fluid flow path flow path between the inlet and the outlet, and having a porous medium interposed between the inlet and the outlet and across the fluid flow path, wherein the housing includes at least one semicircular fluid flow channel that directs fluid from one end to the housing to the substantially opposite end of the housing before contacting the porous medium, and/or wherein the housing includes at least one semicircular fluid flow channel that directs fluid passing through the porous medium to the outlet of the device. In an embodiment, the housing defines a first fluid flow path and a second fluid flow path between the inlet and the outlet, wherein a first porous medium is interposed between the inlet and the outlet and across the first fluid flow path, and a second porous medium is interposed between the inlet and the outlet and across the second fluid flow path, and the housing includes at least one semicircular fluid flow channel that directs fluid from one end to the housing to the substantially opposite end of the housing before contacting the first and second porous medium, and/or wherein the housing includes at least one semicircular fluid flow channel that directs fluid passing through the first and second porous media to the outlet of the device.

An embodiment of a method for processing a biological fluid in accordance with the invention comprises passing a biological fluid into a filter device comprising a housing having an inlet and an outlet and defining a first fluid flow path and a second fluid flow path between the inlet and the outlet, wherein the housing essentially lacks a solid partition between the first fluid flow path and the second fluid flow path; passing a portion of the biological fluid along the first fluid flow path through a first porous medium, the first medium having a first surface and a second surface, interposed between the inlet and the outlet and across the first fluid flow path; passing another portion of the biological fluid along the second fluid flow path through a second porous medium, the second porous medium having a first surface and a second surface, interposed between the inlet and the outlet and across the second fluid flow path.

In a more preferred embodiment, the method includes passing a portion of the biological fluid along the first fluid flow path through a first screen and a first porous medium, the first screen and the first porous medium being interposed between the inlet and the outlet and across the first fluid flow path; passing another portion of the biological fluid along the second fluid flow path through a second screen and a second porous medium, the second screen and the second porous medium being interposed between the inlet and the outlet and across the second fluid flow path.

Another embodiment of a method for processing a biological fluid comprises passing a biological fluid into a filter device comprising a housing having an inlet and an outlet and defining a first fluid flow path and a second fluid flow path between the inlet and the outlet, wherein a first porous medium is interposed between the inlet and the outlet and across the first fluid flow path, and a second porous medium is interposed between the inlet and the outlet and across the second fluid flow path, the device having a space with a changing dimension (e.g., a taper) between the first porous medium and the second porous medium; passing the biological fluid into the space; passing a portion of the biological fluid from the space along the first fluid flow path through the first porous medium and through the outlet; and passing another portion of the biological fluid from the space along the second fluid flow path through the second porous medium and through the outlet.

In another embodiment, wherein the filter device includes a first screen, preferably disposed upstream of the first porous medium, across the first fluid flow path, and a second screen, preferably disposed upstream of the second porous medium, across the second fluid flow path, the method includes passing a portion of the biological fluid from the space along the first fluid flow path through the first screen and the first porous medium and through the outlet; and passing another portion of the biological fluid from the space along the second fluid flow path through the second screen and the second porous medium and through the outlet.

Preferably, the device comprises a leukocyte depletion device, and the method includes depleting leukocytes from the biological fluid.

In some embodiments, the device includes one or more vents such as a gas inlet and/or a gas outlet. Alternatively, or additionally, a system according to the invention includes one or more vents upstream or downstream of the inventive filter device.

Embodiments of a method according to the invention include passing air or gas through one or more vents to separate gas from the biological fluid flow path, and/or to recover biological fluid retained or held up in the device and/or system.

The invention can be used as part of a system, which can be closed or open. In one embodiment of an open system, the filter device is interposed between, and in fluid communication with, at least one container of unfiltered biological fluid and a patient. In other embodiments of closed or open systems, the filter can be interposed between, and in fluid communication with, a plurality of containers. For example, one or more containers upstream of the filter device can be suitable for holding a unit of unfiltered biological fluid, and a container downstream of the filter device can be suitable for holding a unit of filtered biological fluid. In yet another embodiment, the filter device is part of an apheresis system, which is preferably a closed system.

A system can include a plurality of conduits, connectors, additional containers, and one or more flow control devices such as clamps, seals, transfer leg closures or the like. The system can include at least one additional device, including, but not limited to, gas venting devices such as gas storage bags, gas collection and displacement loops, gas inlets, and gas outlets. Suitable gas venting devices include those disclosed in, for example, U.S. Pat. Nos. 5,126,054; 5,217,627, and 5,451,321. In some embodiments, the filter device according to the invention includes one or more gas vents such as gas inlets and/or gas outlets, including those disclosed in the U.S. Patents listed above.

The following definitions are used in accordance with the invention:

(A) Biological Fluid. A biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid; and platelets separated from plasma and resuspended in physiological fluid. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

(B) Porous Medium for treating a biological fluid. A porous medium for treating biological fluid is a medium through which a biological fluid (e.g., blood or blood components) passes. The porous medium has two opposing sides (e.g., an upstream side and an opposing downstream side, in relation to the biological fluid to be treated by being passed through the porous medium, with a central portion therebetween). The porous medium typically removes one or more undesirable substances from the biological fluid. For example, the porous medium can remove photoactive agents (e.g., psoralens, photoactive dyes, methylene blue) and/or their byproducts; coalesced particles; gels; microaggregates; and/or leukocytes.

The porous medium is typically configured as one or more planar or corrugated Glsheets. The porous medium, which can be multilayered, can be a web or a membrane, or combinations thereof. The porous medium may also include one or more structures having different characteristics and/or functions. e.g., leukocyte depletion, as well as prefiltration and/or microaggregate removal. The porous medium can include additional structures such as a mesh, net or screen, on the downstream side and/or upstream side of the porous medium. For example, such an additional structure on the downstream side of the porous medium can provide for support and/or drainage. Alternatively, or additionally, such an additional structure on the upstream side of the porous medium can provide for at least one of filtration, flow distribution, and support.

In some embodiments of devices according to the invention, the device includes a filter across each fluid flow path, wherein the filter includes a plurality of porous media. For example, each filter can comprise a leukocyte depletion element, as well as a prefilter and/or a microaggregate element.

A variety of materials can be used, including a porous synthetic polymeric material, for the first porous medium and the second porous medium. Preferably, the same materials are used for both porous media, even more preferably, both porous media are leukocyte depletion media. Suitable synthetic polymeric material includes, for example, polybutylene terephthalate (PBT), polyethylene, polyethylene terephthalate (PET), polypropylene, polymethylpentene, polyvinylidene fluoride, nylon 6, nylon 66, nylon 612, nylon 11, and nylon 6 copolymers.

In one preferred embodiment, each leukocyte depletion medium comprises a fibrous medium, typically a medium prepared from melt-blown fibers, as disclosed in, for example, U.S. Pat. Nos. 4,880,548; 4,925,572, 5,152,905, and 5,443,743. Each of the media, which can be preformed media, can include a plurality of layers, as disclosed in the U.S. Patents listed above.

The porous media are preferably treated for increased efficiency in processing a biological fluid. For example, each medium may be surface modified to affect the critical wetting surface tension (CWST) of the medium, as described in, for example, the U.S. Patents listed above.

Preferably, the porous media according to the invention, which are, more preferably, porous fibrous media, have a CWST of greater than about 58 dynes/cm. For example, each medium may have a CWST in the range from about 60 dynes/cm to about 115 dynes/cm, e.g., in the range of about 61 to about 100 dynes/cm. In some embodiments, the media have a CWST of about 62 dynes/cm, or greater, e.g., in the range from about 63 to about 70 dynes/cm, or in the range from about 85 dynes/cm to about 98 dynes/cm.

Surface characteristics of the media can be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, electron beam, or to various other forms of radiation, or by surface etching or deposition using a plasma treatment.

Each of the components of the invention will now be described in more detail below, wherein like components have like reference numbers.

In the embodiments illustrated in FIGS. 1A, 1B, 7, 8 and 10, device 100 includes a housing 10, having an inlet 1 and an outlet 2, and defining first and second biological fluid flow paths between the inlet and the outlet. In the embodiment illustrated in FIG. 9, device 100 includes a housing 10, having an inlet 2' and an outlet 1', and defining first and second biological fluid flow paths between the inlet and the outlet. The device 100 as shown in the cross-sectional views of FIGS. 1B, and 7–10 includes a first porous medium 6a and a second porous medium 6b disposed therein, while essentially or completely lacking a solid partition between the porous media 6a, 6b.

Figure 1B:
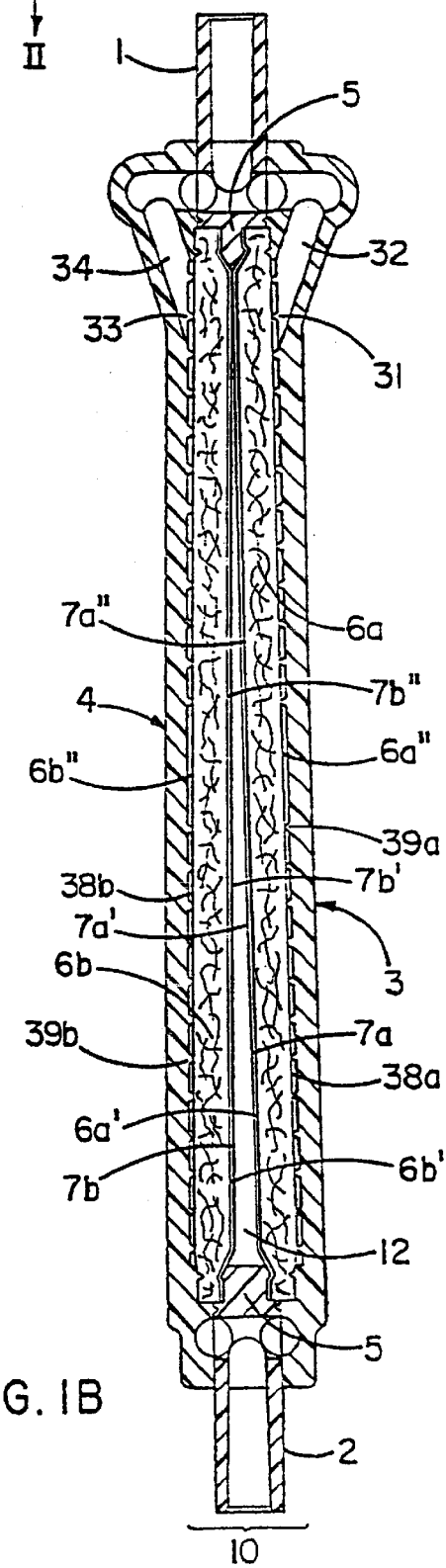
FIG. 1B is an embodiment of the present invention illustrating a cross-sectional side view along line I—I of FIG. 1A showing first and second porous media and first and second elements in a housing, and a space having a diametrically decreasing cross-sectional area between the elements.

In the embodiment shown in FIG. 1B, the device also includes a plurality of elements, i.e., first and second elements 7a, 7b, capable of allowing biological fluid flow therethrough, wherein the elements are interposed between the porous media 6a, 6b. Thus, the cross-sectional view according to FIG. 1B illustrates a first element 7a such as a screen disposed upstream of the first porous medium 6a, wherein the first element and the first porous medium are across the first fluid flow path between the inlet 1 and the outlet 2, and a second element 7b such as a screen disposed upstream of the second porous medium 6b, wherein the second element and the second porous medium are across the second fluid flow path between the inlet 1 and the outlet 2. Suitable elements that are capable of allowing biological fluid flow therethrough include one or more screens, mesh layers, net layers, and perforated plates.

Figure 8:
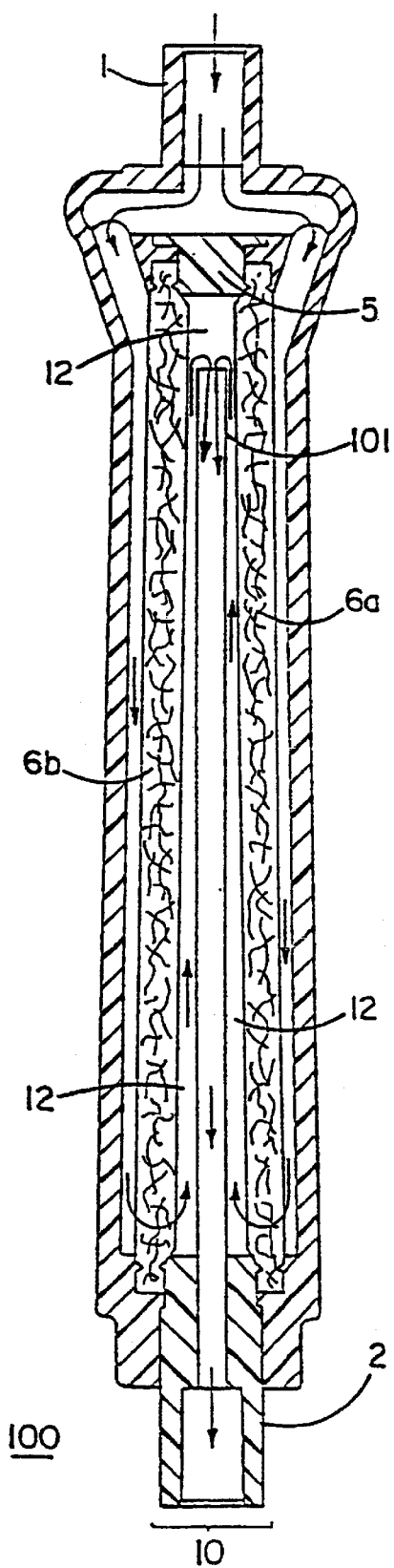
FIG. 8 illustrates the flow of biological fluid through an embodiment of the device illustrated in FIG. 7.

In the embodiments illustrated in FIGS. 7, 8. and 10, the first porous medium 6a is interposed between the inlet 1 and the outlet 2 and across the first biological fluid flow path; and the second porous medium 6b is interposed between the inlet 1 and the outlet 2 and across the second biological fluid flow path. In the embodiment illustrated in FIG. 9, the first porous medium 6a is interposed between the inlet 2' and the outlet 1' and across the first biological fluid flow path; and the second porous medium 6b is interposed between the inlet 1 and the outlet 2 and across the second biological fluid flow path.

In the illustrated embodiments, e.g., as shown in the cross-sectional views according to FIGS. 1B, and 7–10, device 100 also includes a space 12 between the first and second porous media 6a, 6b. Using the cross-sectional view in FIG. 1B for reference, in those embodiments that also include a plurality of additional elements, i.e., elements 7a, 7b interposed between the first and second porous media that allow the flow of biological fluid therethrough, the space 12 is between the first and second elements 7a and 7b. In an embodiment, at least about 50% of the area along the two opposing surfaces of the elements 7a and 7b is bounded by a first surface 7a' of the first element 7a, and a first surface 7b' of the second element 7b.

Figure 10:
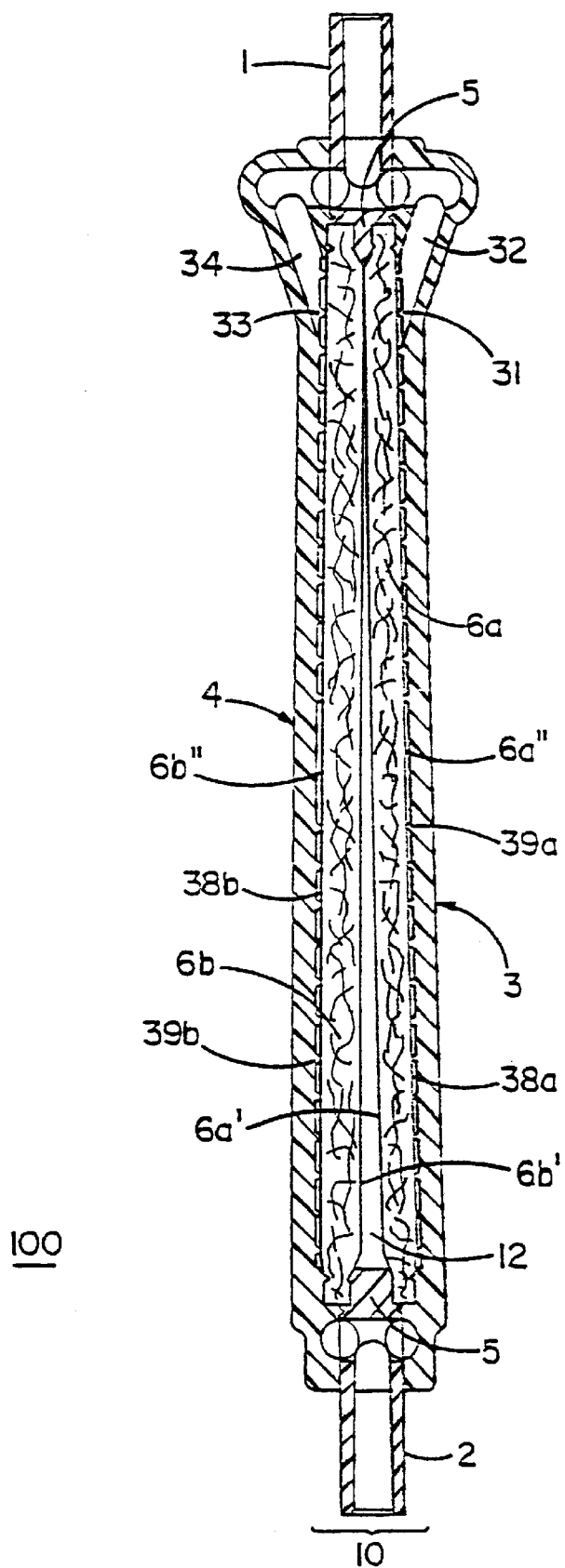
FIG. 10 is another embodiment of the present invention illustrating a cross-sectional side view showing first and second porous media in a housing, and a space having a diametrically decreasing cross-sectional area between the media.

Alternatively, as illustrated in FIG. 10, at least about 50% of the area along the two opposing surfaces of the porous media 6a, 6b can be bounded by a first surface 6a' of the first porous medium 6a, and a first surface 6b' of the second porous medium 6b.

In some embodiments, the space 12 has a changing dimension (e.g., decreasing area and/or volume) from one portion of the device to another. For example, the space can be tapered, i.e., the first and second elements 7a, 7b (FIG. 1B) or the first and second porous media 6a, 6b (FIG. 10) extend at an angle from one another. The first and second elements 7a, 7b (FIG. 1B) or the first and second porous media 6a, 6b (FIG. 10) can contact each other along a minor area, or there can be no contact between the media.

The device 100 can be fashioned in a variety of configurations and shapes. An exemplary configuration includes three housing sections, i.e., a manifold section 5, providing a common inlet flow path along one portion and a common outlet flow path along another portion; a first outlet section 3; and a second outlet section 4. Typically, first element 7a and first porous medium 6a are sealed between manifold section 5 and first outlet section 3, and second element 7b and second porous medium 6b are sealed between manifold section 5 and second outlet section 4. Of course, in those embodiments lacking first and second elements 7a, 7b, the porous media 6a, 6b can be sealed between the manifold section and the respective outlet section.

Figure 2A:
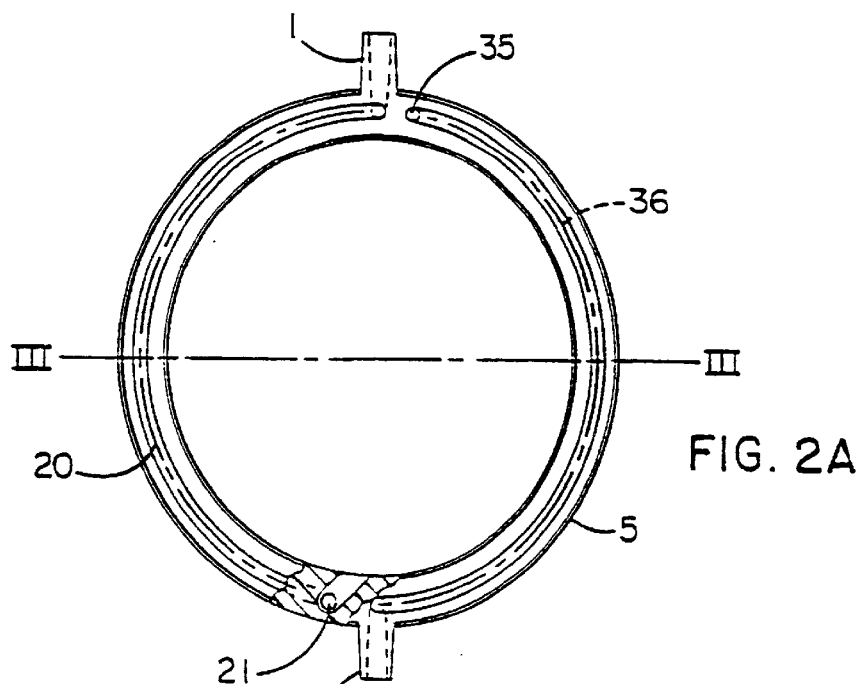
FIG. 2A illustrates an elevation view of an inlet fluid flow channel leading to the first and second porous media according to an embodiment of the present invention.
Figure 2C:
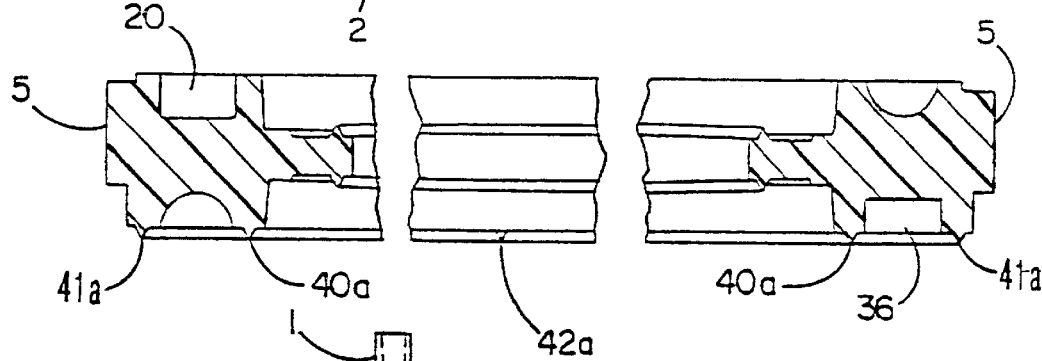
FIG. 2C illustrates a cross-sectional view of FIG. 2A along line III—III according to an embodiment of the present invention.
Figure 2B:
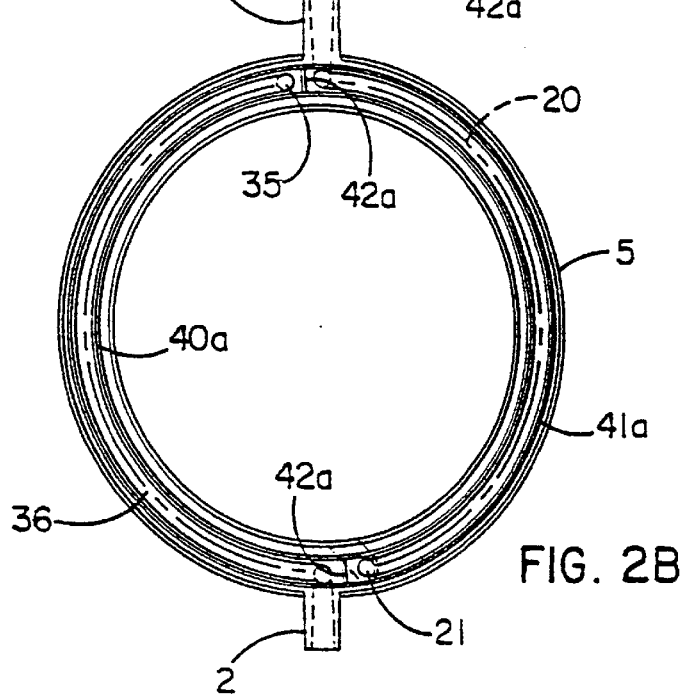
FIG. 2B illustrates an elevation view of a common outlet fluid flow channel leading to the outlet according to an embodiment of the present invention.

In the embodiment illustrated in FIGS. 2A and 2B, manifold section 5 provides a common inlet flow path from inlet 1 along inlet channel 20 to port or slot 21 and then to space 12 (FIG. 1B and FIG. 10) where the fluid flow path is separated into the first fluid flow path and the second fluid flow path. For example, using FIG. 1B for reference, the first fluid flow path passes through first element 7a and first porous medium 6a, and the second fluid flow path passes through second element 7b and second porous medium 6b. After the biological fluid is filtered through the first or second porous media 6a, 6b, and passes through sections 3 or 4 (FIGS. 3 and 4) into common outlet port 35 of manifold section 5 (FIG. 2B), the manifold section provides a common outlet flow path from port 35 along outlet channel 36 to outlet 2.

In some embodiments, e.g., as illustrated in FIGS. 2A and 2B, the fluid flow channels 20 and 36 are circumferentially or semicircularly disposed in manifold section 5, wherein channel 20 directs fluid from the inlet 1 to port or slot 21, and channel 36 direct fluid from common outlet port 35 toward the outlet 2. If desired, as shown in FIG. 2C, the fluid flow channels 20 and 36 can be formed along opposing faces of the manifold section.

In the embodiment illustrated in FIG. 3, first outlet section 3 includes a surface having a slot 37a, and a plurality of channels 38a and ridges 39a. The ridges 39a provide clearance between the internal surface of the first outlet section 3 and the second surface 6a" of the first porous medium 6a. In some embodiments, this clearance allows filtered biological fluid to be directed more efficiently along slot 37a, channels 38a and through port 31 (FIG. 3) and passageway 32 (FIG. 1B), before it passes into common port 35 of manifold section 5 (FIG. 2B).

Similarly, as illustrated in FIG. 4, second outlet section 4 includes a surface having a slot 37b, and a plurality of channels 38b and ridges 39b, which, in some embodiments, allows filtered biological fluid to be directed more efficiently along slot 37b, channels 38b and through port 33 (FIG. 4) and passageway 34 (FIG. 1B), before it passes into common port 35 of manifold section 5 (FIG. 2B).

If desired, the device can also include at least one sealing arrangement that allows efficient fluid communication between sections while further minimizing the chance of contaminating the filtered fluid with the unfiltered fluid. Illustratively, a sealing arrangement can include at least one, and typically a plurality, of ridges, bosses, beads, and/or ribs. At least a portion of the sealing arrangement (e.g., one or more ridges or ribs) is typically located to contact at least one surface of an element 7a, 7b, and/or at least one surface of a porous medium 6a, 6b when the sections of the housing are sealed together. If desired, at least a portion of the sealing arrangement, e.g., at least one ridge or rib, can be bonded to the element(s) and/or media, e.g., near the periphery of the surfaces of the elements (7a', 7b', 7a", 7b") or the porous media (6a', 6b", 6a", 6b"), to provide for a fluid tight seal.

Exemplary sealing arrangements are illustrated in FIGS. 2B and 3, showing ribs 40a, 41a, and 42a (FIG. 2B), and ribs 40b, 41b, and 42b (FIG. 3). FIGS. 2B and 3 illustrate inner circumferential ribs 40a and 40b, outer circumferential ribs 41a and 41b, and transverse ribs 42a and 42b.

Using FIGS. 1B and 2B for reference, the contact between the ribs 40a, 41a, and 42a (FIG. 2B), and the first element 7a (FIG. 1B) provides a seal to further minimize the chance of contaminating the filtered filed with the unfiltered fluid, since the seal further prevents unfiltered fluid from passing from inlet channel 20 into outlet channel 36 (FIG. 2B).

Similarly, using FIGS. 1B, 2A and 3 for reference, the contact between the ribs 40b, 41b, and 42b (FIG. 3), and the first element 7a (FIG. 1B) provides a seal to further minimize the chance of contaminating the filtered fluid with the unfiltered fluid, since the seal further prevents unfiltered fluid from passing from inlet channel 20 into outlet channel 36 (FIG. 2A).

In other embodiments (not shown), manifold section 5 includes a sealing arrangement on each side of the section. Alternatively, or additionally, the first outlet section 3 and the second outlet section 4 can both include a sealing arrangement.

Of course, a variety of other suitable sealing arrangements for sealing the elements and porous media within the housing are included within the scope of the invention. Illustratively, one embodiment of the device also includes at least one hollow nipple that allows efficient fluid communication between sections while minimizing contamination. For example, as illustrated in FIG. 11, outlet section 3 includes a nipple 50, that can be tapered, at one end of passageway 32 that contacts the walls of port 35. The contact between nipple 50 and the walls of port 35 provides a seal to further minimize the chance of contaminating the filtered fluid with the unfiltered fluid, since the seal further prevents unfiltered fluid from passing from inlet channel 20 into outlet channel 36. In another embodiment (not shown), both outlet sections include nipples that contact the walls of port 35.

Since every cubic centimeter (cc) of biological fluid can be valuable, and the fluid held up or retained in the filter after filtration can be "lost" in the sense that it is not recovered for administration to the patient, the filter device 100 according to the invention preferably minimizes fluid hold up. In preferred embodiments, particularly involving the filtration of two or more units of biological fluid, the device holds up about 85 cc or less of biological fluid, more preferably, about 70 cc or less, even more preferably, about 50 cc or less.

The space 12 between first and second porous media 6a, 6b, in the device can be modified to provide a desired hold up volume. For example, using FIG. 1B for reference, wherein first element 7a is disposed upstream of first porous medium 6a, and second element 7b is disposed upstream of second porous medium 6b, the space 12 between the first surface 7a' of the first element 7a and the first surface 7b' of the second element 7b can be reduced. Illustratively, FIG. 1B shows the diametric cross-sectional area of the space 12 decreasing from one end of the device to another. In those embodiments lacking elements 7a and 7b (e.g., as shown in FIG. 10), the space 12 between the first surface 6a' of the first porous medium 6a and the first surface 6b' of the second porous medium 6b can be similarly reduced.

In some embodiments the space 12 can be reduced by utilizing a tapered configuration. For example, in the embodiment illustrated in FIG. 1B, the space is tapered and the first surface 7a' of the first element 7a and the first surface 7b' of the second element 7b contact each other along a minor area. Alternatively, as illustrated in, for example, FIG. 10, the space is tapered and the first surface 6a' of first porous medium 6a and the first surface 6b' of second porous medium 6b contact each other along a minor area. In addition to reducing the hold up volume, the use of a space with changing dimension (e.g., a tapered space having an increased area where the biological fluid enters the space) may also be advantageous as it allows material such as gels and/or microaggregates to accumulate in the space while minimizing the effect on filtering efficiency. This can be particularly desirable for those embodiments that include filtering stored biological fluid, e.g., stored packed red cells.

Another advantage of using a space, whether it is tapered or non-tapered, it that the more dense undesirable material, e.g., gels, can accumulate at the lower portion of the space, while minimizing the effect on filtering efficiency.

In a preferred embodiment, the device should be configured to provide efficient air or gas clearance, preferably by allowing the device to fill from the bottom. This configuration directs biological fluid so that it contacts the porous media 6a, 6b near the bottom of the space 12, and allows the housing to fill from the bottom. The rising front of biological fluid forces air to the top of the housing, and the air is passed out of the outlet 2 ahead of the rising level of the biological fluid.

A variety of device housing shapes are suitable for carrying out the invention. For example, the housing may be generally circular, oval, triangular, rectangular or square in shape. In some embodiments, e.g., wherein the filter device is part of a system including one or more blood bags, and the system is centrifuged, a generally circular or oval planar shape can be preferable. For example, a circular or oval planar device can be easier to fit in the centrifuge cup with a plurality of blood bags, and/or the circular or oval shape minimizes or eliminates corners that can contact and damage the blood bag during centrifugation.

The housing 10 can be fabricated from any suitable rigid impervious material, including any impervious thermoplastic material, which is compatible with the biological fluid being processed. For example, the housing can be a polymer, more preferably a transparent or translucent polymer, such as an acrylic, polypropylene, polystyrene, or a polycarbonated resin. Such a housing is easily and economically fabricated, and allows observation of the passage of the biological fluid tough the housing.

The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

A variety of techniques for sealing, fitting, and/or bonding the first and second porous media (and the first and second elements) within or to the housing are suitable. Similarly, a variety of techniques for sealing, fitting, and/or bonding one section of the housing to the other are suitable. For example, the media and elements can be compression sealed or interference fit within the housing. The media and elements can be bonded to the housing. Preferably, the sections of the housing are welded together, e.g., heat welded or ultrasonically welded. In one embodiment, the circumferential edges of the media and/or elements are sealed between housing sections when the sections are secured together, e.g., by ultrasonic welding.

In another embodiment of the invention (not shown), the filter device includes one or more vents such as a gas inlet and/or a gas outlet. For example, the device can include at least one gas inlet and/or gas outlet including at least one microporous membrane capable of passing gas therethrough to allow air to enter the device and/or exit the device. The membrane, that includes one or more liquophobic layers, and can also include one or more liquophilic layers, typically has a pore structure that prevents the passage of biological fluid therethrough under the pressure differential created in conventional biological fluid processing protocols. Typically, the membrane has a pore size that prevents bacteria from entering the device, e.g., a pore size of about 0.2 micrometers or less. Suitable vents, including gas inlets and gas outlets, are disclosed in, for example, U.S. Pat. Nos. 5,126,054, 5,217,627, and 5,451,321.

In one embodiment, the device includes two gas outlets, e.g., wherein the first outlet section 3 and the second outlet section 4 each include a microporous liquophobic membrane that allows air to pass through and exit the device. In another embodiment, the device includes a single gas outlet, e.g., communicating with outlet channel 36.

The device can include one or more gas inlets. For example, the device can include a microporous liquophobic membrane communicating with inlet channel 20 that allows air to pass through and enter the device, e.g., to displace biological fluid from the device.

In an embodiment, the filter device includes at least one gas inlet, and at least one gas outlet. Alternatively, or additionally, the system including the filter device can include separate gas inlets and/or gas outlets, e.g., upstream and downstream of the inventive filter device. In some embodiments, the device and/or system can include a cap for at least one outlet and/or inlet.

In one embodiment including at least one gas outlet, the outlet comprises at least one liquophobic layer and at least one liquophilic layer, with the liquophilic layer disposed to contact the biological fluid. Air inside the housing passes from the device through the liquophilic and liquophobic layers until the liquophilic layer is wetted with the biological fluid. Once the liquophilic layer is wetted, gas flow stops, without biological fluid passing through the liquophobic layer.

Embodiments of the method according to the invention can be carried out in a wide variety of biological fluid processing protocols, and with closed or open systems. For example, biological fluid, e.g., donated blood, can be collected in a blood bag, and filtered through the device according to the invention during initial processing by a blood bank and/or during bedside administration of blood or blood components. The biological fluid can be separated into components, e.g., after collection in a blood bag, or during apheresis, and one or more of the separated components can be filtered through the inventive device.

In accordance with preferred embodiments of the method, unfiltered biological fluid contacts the elements 7a, 7b, and porous media 6a, 6b, near the bottom of the space 12 and the biological fluid is filtered as it passes through the media 6a, 6b. In some of the embodiments wherein the elements 7a and 7b are disposed upstream of the porous media 6a and 6b, the elements 7a and 7b also provide for some filtration, e.g., to remove larger particles and/or debris.

This configuration, i.e., allowing the fluid to contact the elements and porous media near the bottom of the space 12, minimizes the formation of air pockets, and allows both media 6a, 6b, to be efficiently wetted. Furthermore, the front of biological fluid rising in the device efficiently displaces the air, and forces the air out of the outlet 2 ahead of the rising level of the biological fluid.

Using FIGS. 1B and 2A for reference, the biological fluid to be filtered enters inlet 1 at one end of the device, and passes along channel 20 through port 21 at the opposite, or nearly opposite, end of the device. Thus, unfiltered biological fluid can pass from one end of the device to the nearly opposite end before passing through port 21, into space 12, and contacting the elements 7a, 7b, and porous media 6a, 6b.

Biological fluid exiting port 21 into space 12 passes along one of two fluid flow paths as follows:

A portion of biological fluid passes along a first fluid flow path from the first surface 7a' through the second surface 7a" of first element 7a. Fluid continues along the first fluid flow path and passes from the first surface 6a' through the second surface 6a" of first porous medium 6a. Using FIGS. 1B and 3 for reference, fluid exiting second surface 6a" passes along channel 37a, channels 38a, and through port 31, passageway 32, and then (as shown in FIG. 2A) into common port 35.

Referring again to FIG. 1B, another portion of biological fluid passes along a second fluid flow path from the first surface 7b' through the second surface 7b" of second element 7b. Fluid continues along the second fluid flow path and passes from the first surface 6b' through the second surface 6b" of second porous medium 6b. Referring now to FIGS. 1B and 4, fluid exiting second surface 6b" passes along channel 37b, channels 38b, and then (as shown in FIG. 2B) through port 33, passageway 34, and into common port 35.

Continuing to refer to FIG. 2B, the filtered fluid passing into common port 35 passes along common outlet channel 36 to outlet 2, and is subsequently collected in a container such as a satellite blood bag and/or administered to a patient.

In some embodiments, e.g., wherein the inventive device is utilized as part of an apheresis system, a fluid such as air from the centrifuge bowl can be used to "chase" biological fluid (e.g., red blood cell containing- or platelet-containing fluid) from the device, to allow the additional biological fluid to be recovered in the downstream container.

In one embodiment, two or more units of biological fluid, e.g., two or more units of packed red blood cells or platelet concentrate, are passed through the same device and administered to a patient at bedside.

In another embodiment, e.g., involving apheresis, especially plateletpheresis or erythrocytapheresis, the desired component from a single donor is passed through the device. The device is also suitable for those apheresis protocols involving the collection of a "double" or a "triple" unit of platelets from a single donor. A variety of apheresis protocols are suitable for carrying out the invention. Suitable apheresis protocols include, but are not limited to, those disclosed in U.S. Pat. No. 5,545,339.

Typically, in those embodiments including venting, a flow control device such as a clamp or valve downstream of the filter device is closed and opened during the processing protocol. For example, a flow control device associated with a conduit in fluid communication with the outlet of the filter device is typically closed before biological fluid is passed into the filter device. As the filter device fills with biological fluid, gas or air is displaced and passed through one or more gas outlet(s). Once the filter device is primed, the flow control device is opened, and the filtered biological fluid passes from the device to, for example, a patient or a satellite bag. If desired, biological fluid held up in the device and/or conduits communicating with the device can be recovered by passing gas through one or more gas inlet(s) into the filter device. For example, the air or gas passing through the gas inlet(s) drives additional biological fluid from the filter device into the satellite bag.

In accordance with embodiments of the invention, a structure (that can be permeable or impermeable to biological fluid flow) can be interposed in the space 12 between the first and second media 6a, 6b, along a minor area between first surface 6a' and first surface 6b', or between first surface 7a' (of first element 7a) and first surface 7b' (of second element 7b). As used herein, minor area refers to less than about 50%, e.g., in the range of from about 40% to about 25%, of the area between the surfaces 6a', 6b' or 7a', 7b'. Typically, however, the device essentially lacks a solid partition plate (a plate that does not allow the flow of biological fluid therethrough) between the first fluid flow path and the second fluid flow path. As used herein, essentially lacking refers to about 15% or less, e.g., about 5% or less, about 3% or less, or about 1% or less, of the area between the first and second flow paths.

In accordance with some embodiments of the invention, as noted above, a structure capable of allowing biological fluid flow therethrough can interposed between the first and second fluid flow paths. In an embodiment, the structure(s) capable of allowing biological fluid flow therethrough are interposed along more than about 60% of the area between the first and second fluid flow paths. In another embodiment, the structure capable of allowing biological fluid flow therethrough is interposed along a minor area between the surfaces 6a', 6b' or 7a', 7b'.

In other embodiments, one or more conduits, e.g., flexible plastic tubes, are included to direct flow into, through, and/or out of, the device. For example, two or more PVC tubes can be connected in the form of a "Y" or a "T" to direct biological fluid to the space between the porous media, and/or to direct the filtered fluid passing from the media to the outlet. Conduits can be external and/or internal to the housing, and flow can be "inside/out" (from the space to the porous media) or "outside/in" (from the media to the space).

Figure 9:
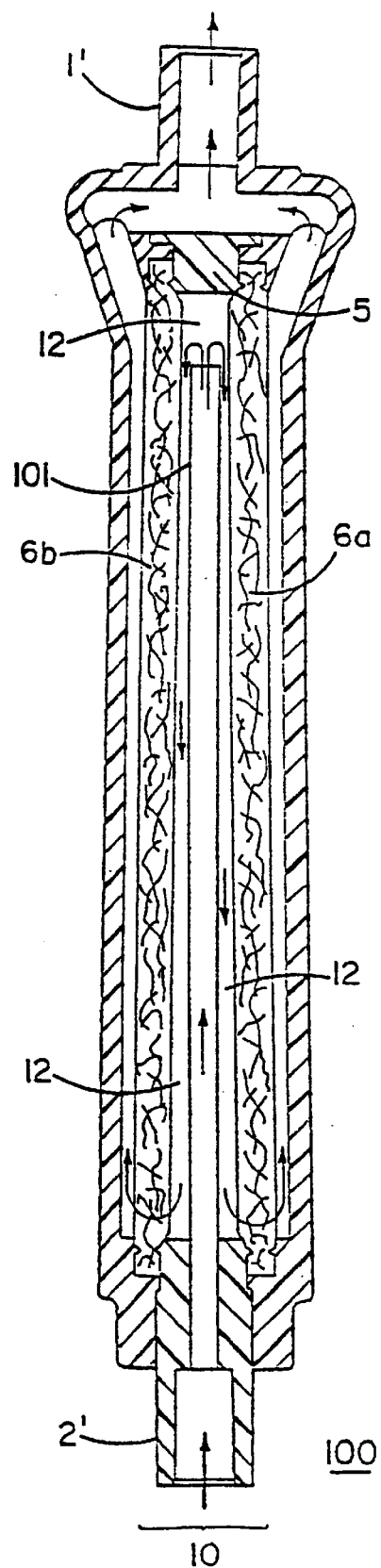
FIG. 9 illustrates the flow of biological fluid through another embodiment of the device illustrated in FIG. 7.

In some embodiments, as illustrated in FIGS. 7–9, the device includes a conduit 101 having one end leading to the space 12 and the other end leading to the outlet (FIG. 8) or the inlet (FIG. 9) of the device. The arrows in FIGS. 8 and 9 illustrate flow of the biological fluid.

For example, as illustrated in FIG. 8, biological fluid enters the device through inlet 1, and a portion of the biological fluid passes through porous medium 6a into space 12, and another portion of the biological fluid passes through porous medium 6b into space 12. As the device fills with biological fluid, the level of fluid will approach the end of conduit 101 in space 12. The fluid will eventually rise above this end of the conduit, and will then pass through the conduit to the other end, communicating with outlet 2. Thus, the conduit 101 directs the filtered fluid from the space 12 through the outlet 2.

In the embodiment illustrated in FIG. 9, the conduit 101 directs the unfiltered fluid from the inlet 2' into the space 12. Biological fluid enters the device through inlet 2', and one end of conduit 101. The biological fluid passes through the conduit 101, and exits the other end of the conduit into space 12. A portion of the biological fluid passes through porous medium 6a, and another portion of the biological fluid passes through porous medium 6b. As the device fills with fluid, filtered biological fluid passes from the device through outlet 11.

In variations of the embodiments illustrated in FIGS. 8 and 9, additional elements that allow the passage of biological fluid therethrough can be disposed along the fluid flow paths. For example, additional elements such as screen or mesh layers can be disposed upstream of the first and second porous media, so that the portion of biological fluid passes through the mesh or screen before it passes through the porous medium.

A variety of other configurations are encompassed by the invention. For example, the housing can be configured to provide an inlet and an outlet near the same end, e.g., the top, of the housing. Such a configuration can be especially advantageous for use in a centrifuge. One embodiment of this configuration is illustrated in FIG. 6, with the inlet channel 20 and the outlet channel 36 formed along opposing faces of the manifold section 5. Thus, the biological fluid passes along first and second fluid flow paths through the first and second porous media, passes through common port 35, and along common outlet channel 36 to outlet 2.

In accordance with another embodiment of the invention, a biological fluid filter device comprises a housing having an inlet and an outlet and defining at least one fluid flow path flow path between the inlet and the outlet, and having a porous medium interposed between the inlet and the outlet and across the fluid flow path, wherein the housing includes at least one semicircular fluid flow channel that directs fluid from one end to the housing to the substantially opposite end of the housing before contacting the porous medium and/or directs the fluid passing through the porous medium to the outlet of the device. For example, the device can include a semicircular fluid flow channel that directs fluid from one end to the housing to the substantially opposite end of the housing before contacting the porous medium and includes another semicircular fluid flow channel that directs the fluid passing through the porous medium to the outlet of the device. The device can comprise a housing having an inlet and an outlet and defining a first fluid flow path and a second fluid flow path between the inlet and the outlet, and first and second porous media interposed between the inlet and the outlet and across the respective fluid flow paths as described earlier.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A biological fluid filter device comprising:
   a housing having an inlet and an outlet and defining a first fluid flow path and a second fluid flow path between the inlet and the outlet, wherein the housing essentially lacks a solid partition between the first fluid flow path and the second fluid flow path;
   a first porous element, comprising a leukocyte depletion medium, having a first surface and a second surface, interposed between the inlet and the outlet and across the first fluid flow path;
   a second porous element, comprising a leukocyte depletion medium, having a first surface and a second surface, interposed between the inlet and the outlet and across the second fluid flow path; and a space between the first porous element and the second porous element, the first surface of the first porous element opposing, and, for at least a portion of said surface spaced apart from, the first surface of the second porous element.

2. The device of claim 1, wherein the device includes at least one fluid flow channel directing fluid from the inlet at one end of the housing to the substantially opposite end of the housing before contacting the first porous element and the second porous element.

3. The device of claim 2, wherein the housing further includes at least one semicircular fluid flow channel that directs the fluid passing through the first porous element and the second porous element to the outlet of the device.

4. The device of claim 1, including a semicircular fluid flow channel providing fluid communication between the inlet and the space between the first and second porous elements.

5. The device of claim 1, including a semicircular fluid flow channel providing fluid communication between the second surfaces of the first and second porous elements and the outlet.

6. The device of claim 1, wherein the device includes one or more fluid flow channels that direct the fluid passing through the first porous element and the second porous element from one end of the housing to the substantially opposite end of the housing.

7. The device of claim 1, wherein the first porous element and the second porous element contact one another along a minor area.

8. The device of claim 1, including an element capable of passing biological fluid therethrough interposed between the first porous element and the second porous element.

9. The device of claim 1 wherein the space is tapered.

10. The device of claim 1 including at least one semicircular flow channel.

11. The device of claim 1 including at least one vent comprising a porous membrane that allows gas to pass therethrough.

12. The device of claim 11, wherein the vent comprises a gas inlet including a liquophobic membrane.

13. The device of claim 11, wherein the vent comprises a gas outlet including a liquophobic membrane.

14. A biological fluid filter device comprising:

a housing having an inlet and an outlet and defining a first fluid flow path and a second fluid flow path between the inlet and the outlet, wherein the housing essentially lacks a solid partition between the first fluid flow path and the second fluid flow path;

a first element capable of allowing biological fluid flow therethrough, having a first surface and a second surface, and a first leukocyte depletion medium, having a first surface and a second surface, the first element and the first leukocyte depletion medium being interposed between the inlet and the outlet and across the first fluid flow path;

a second element capable of allowing biological fluid flow therethrough, having a first surface and a second surface, and a second leukocyte depletion medium, having a first surface and a second surface, the second element and the second leukocyte depletion medium being interposed between the inlet and the outlet and across the second fluid flow path; and a space between the first element and the second element, the first surface of the first element opposing, and, for at least a portion of said surface spaced apart from, the first surface of the second element.

15. The device of claim 14, wherein the first surface of the first element contacts the first surface of the second element along a minor area.

16. The device of claim 14, wherein the first element and the second element each comprise a screen.

17. A biological fluid filter device comprising:

a housing having an inlet and an outlet and defining a first fluid flow path and a second fluid flow path between the inlet and the outlet, wherein the housing essentially lacks a solid partition between the first fluid flow path and the second fluid flow path;

a first filter, having a first surface and a second surface, interposed between the inlet and the outlet and across the first fluid flow path, the first filter comprising a leukocyte depletion element, and at least one of a prefilter element and a microaggregate element;

a second filter, having a first surface and a second surface, interposed between the inlet and the outlet and across the second fluid flow path the second filter comprising a leukocyte depletion element and at least one of a prefilter element and a microaggregate element; and a space between the first filter and the second filter, the first surface of the first filter opposing, and, for at least a portion of said surface spaced apart from, the first surface of the second filter.

18. A biological fluid filter device comprising:

a housing having an inlet and an outlet and defining a first fluid flow path and a second fluid flow path between the inlet and the outlet, wherein the housing essentially lacks a solid partition between the first fluid flow path and the second fluid flow path;

a first filter, having a first surface and a second surface, interposed between the inlet and the outlet and across the first fluid flow path, the first filter comprising a leukocyte depletion element and a prefilter element;

a second filter, having a first surface and a second surface, interposed between the inlet and the outlet and across the second fluid flow path, the second filter comprising a leukocyte depletion element and a prefilter element; and a tapered space between the first filter and the second filter, the first surface of the first filter opposing, and, for at least a portion of said surface spaced apart from, the first surface of the second filter.

19. The device of claim 18, wherein the first filter and the second filter contact one another along a minor area.

20. The device of claim 18, including at least first and second elements capable of allowing biological fluid flow therethrough, interposed between the first filter and the second filter, wherein the first element is disposed across the first fluid flow path, and the second element is disposed across the second fluid flow path.

21. The device of claim 18, wherein the first filter and the second filter each further comprises a microaggregate element.

22. A biological fluid filter device comprising:

a housing having an inlet and an outlet and defining a first fluid flow path and a second fluid flow path between the inlet and the outlet, wherein the housing essentially lacks a solid partition between the first fluid flow path and the second fluid flow path;

a first porous medium, having a first surface and a second surface, interposed between the inlet and the outlet and across the first fluid flow path, the first porous medium comprising a leukocyte depletion medium;

a second porous medium, having a first surface and a second surface, interposed between the inlet and the outlet and across the second fluid flow path, the second porous medium comprising a leukocyte depletion medium; and at least one planar element capable of allowing biological fluid flow therethrough, interposed between the first porous medium and the second porous medium.

23. The device of claim 22, wherein the planar element comprises a screen.

24. A biological fluid filter device comprising:

a housing having an inlet and an outlet and defining at least one fluid flow path between the inlet and the outlet, and having a porous medium interposed between the inlet and the outlet and across the fluid flow path, wherein the housing includes at least one semicircular fluid flow channel that directs fluid from one end to the housing to the substantially opposite end of the housing before contacting the porous medium.

25. The device of claim 24, including a filter element, the filter element comprising the first porous medium.

26. The device of claim 25, wherein the filter element comprises a leukocyte depletion medium.

27. The device of claim 24, wherein the housing further includes at least one semicircular fluid flow channel that directs the fluid passing through the porous medium to the outlet of the device.

28. A biological fluid filter device comprising:

a housing having an inlet and an outlet and defining at least one fluid flow path between the inlet and the outlet, and having a porous medium interposed between the inlet and the outlet and across the fluid flow path, wherein the housing includes at least one semicircular fluid flow channel that directs the fluid passing through the porous medium to the outlet of the device.

29. The device of claim 28, including a filter element, the filter element comprising the first porous medium.

30. The device of claim 29, wherein the filter element comprises a leukocyte depletion medium.

31. A method for processing a biological fluid comprising:

passing a biological fluid into a filter device comprising a housing having an inlet and an outlet and defining a first fluid flow path and a second fluid flow path between the inlet and the outlet, wherein the housing essentially lacks a solid partition between the first fluid flow path and the second fluid flow path;

passing a portion of the biological fluid along the first fluid flow path through a first porous element, comprising a leukocyte depletion medium, the first porous element having a first surface and a second surface, interposed between the inlet and the outlet and across the first fluid flow path;

passing another portion of the biological fluid along the second fluid flow path through a second porous element, comprising a leukocyte depletion medium, the second porous element having a first surface and a second surface, interposed between the inlet and the outlet and across the second fluid flow path.

32. The method of claim 31 wherein the device also includes a first additional element for passing biological fluid therethrough across the first fluid flow path, and a second additional element for passing biological fluid therethrough across the second fluid flow path, and the method including passing a portion of the biological fluid along the first fluid flow path through the first additional element and the first porous element, and passing another portion of biological fluid along the second fluid flow path through the second additional element and the second porous element.

33. The method of claim 31, wherein the method includes passing more than one unit of biological fluid through the device.

34. The method of claim 31, wherein the biological fluid comprises packed red blood cells.

35. The method of claim 31, including passing the biological fluid along a semicircular fluid flow path between the inlet of the device and the first porous element and the second porous element.

36. The method of claim 31 including passing gas through at least one microporous membrane.

37. The method of claim 31 including passing gas into the device through at least one gas inlet.

38. The method of claim 37, including recovering additional biological fluid after the gas passes through the gas inlet.

39. The method of claim 31, wherein the device includes at least one additional element suitable for passing biological fluid therethrough interposed between the first porous element and the second porous element, and the method includes passing at least a portion of the biological fluid through the additional element.

40. A method for processing a biological fluid comprising:

passing a biological fluid into a filter device comprising a housing having an inlet and an outlet and defining a first fluid flow path and a second fluid flow path between the inlet and the outlet, wherein a first porous medium comprising a first leukocyte depletion medium is interposed between the inlet and the outlet and across the first fluid flow path, and a second porous medium comprising a second leukocyte depletion medium is interposed between the inlet and the outlet and across the second fluid flow path, the device having a tapered space between the first porous medium and the second porous medium;

passing the biological fluid into the tapered space;

passing a portion of the biological fluid from the space along the first fluid flow path through the first porous medium and through the outlet; and passing another portion of the biological fluid from the space along the second fluid flow path through the second porous medium and through the outlet.

41. A method for processing biological fluid comprising:

passing a biological fluid through a filter device comprising a housing having an inlet and an outlet and defining at least one fluid flow path between the inlet and the outlet, and having a porous medium interposed between the inlet and the outlet and across the fluid flow path, wherein passing the fluid through the device includes passing the fluid along at least one semicircular fluid flow channel from one end to the housing to the substantially opposite end of the housing before the fluid contacts the porous medium.

42. The method of claim 41, wherein the device includes a leukocyte depletion filter element comprising the porous medium, and the method includes passing the biological fluid through the leukocyte depletion filter element and depleting leukocytes from the biological fluid.

43. The method of claim 42, including passing the biological fluid along at least one semicircular fluid flow channel from the leukocyte depletion filter element to the outlet of the device.

44. A method for processing biological fluid comprising:

passing a biological fluid through a filter device comprising a housing having an inlet and an outlet and defining at least one fluid flow path between the inlet and the outlet, and having a porous medium interposed between the inlet and the outlet and across the fluid flow path, wherein passing the fluid through the device includes passing the fluid along at least one semicircular fluid flow channel from the porous medium to the outlet of the device.

45. The method of claim 44, wherein the device includes a leukocyte depletion filter element comprising the porous medium, and the method includes passing the biological fluid through the leukocyte depletion filter element and depleting leukocytes from the biological fluid.

46. A method for processing a biological fluid comprising:

passing a biological fluid into a filter device comprising a housing having an inlet and an outlet and defining a first fluid flow path and a second fluid flow path between the inlet and the outlet, wherein the housing essentially lacks a solid partition between the first fluid flow path and the second fluid flow path;

passing a portion of the biological fluid along the first fluid flow path through a first filter, the first filter having a first surface and a second surface, interposed between the inlet and the outlet and across the first fluid flow path, the first filter comprising a leukocyte depletion element and at least one of a prefilter element and a microaggregate element;

passing another portion of the biological fluid along the second fluid flow path through a second filter, the first filter having a first surface and a second surface, interposed between the inlet and the outlet and across the second fluid flow path, the second filter comprising a leukocyte depletion element and at least one of a prefilter element and a microaggregate element.

47. A method for processing a biological fluid comprising:

passing a biological fluid into a filter device comprising a housing having an inlet and an outlet and defining a first fluid flow path and a second fluid flow path between the inlet and the outlet, wherein the housing essentially lacks a solid partition between the first fluid flow path and the second fluid flow path, the device including a first porous medium including a first leukocyte depletion element, a second porous medium including a second leukocyte depletion element, and a planar element capable of allowing biological fluid therethrough, the element being interposed between the first porous medium and the second porous medium, wherein the first porous medium, the second porous medium, and the planar element are interposed between the inlet and the outlet;

passing the biological fluid through the planar element;

passing a portion of the biological fluid along the first fluid flow path through the first porous medium, the first medium having a first surface and a second surface, interposed between the inlet and the outlet and across the first fluid flow path;

passing another portion of the biological fluid along the second fluid flow path through the second porous medium, the second porous medium having a first surface and a second surface, interposed between the inlet and the outlet and across the second fluid flow path.

* * * * *